United States Patent [19]

Inamoto et al.

[11] 4,070,540
[45] Jan. 24, 1978

[54] 4-HOMOISOTWISTANE-3-CARBOXYLIC ACID ESTERS AND A PROCESS FOR PRODUCING THE SAME

[75] Inventors: Yoshiaki Inamoto; Yoshiaki Fujikura; Hiroshi Ikeda, all of Wakayama; Naotake Takaishi, Iwade, all of Japan

[73] Assignee: Kao Soap Co., Ltd., Tokyo, Japan

[21] Appl. No.: 695,976

[22] Filed: June 14, 1976

[30] Foreign Application Priority Data

June 24, 1975 Japan .................................. 50-78221

[51] Int. Cl.$^2$ .............................................. C07C 69/74
[52] U.S. Cl. .............................. 560/117; 260/514 G; 424/305

[58] Field of Search ....................... 260/468 G, 514 G

[56] References Cited

PUBLICATIONS

Aigami et al., J. Med. Chem. 19, 530 (1976).
Takaishi et al., Chem. Comm. 371 (1975).
March, Advanced Organic Chem. pp. 319–320, (1909).

*Primary Examiner*—Robert Gerstl
*Attorney, Agent, or Firm*—Oblon, Fisher, Spivak, McClelland & Maier

[57] ABSTRACT

4-homoisotwistane-3-carboxylic acid esters have been prepared and shown to possess superior antiviral effects.

5 Claims, No Drawings

4-HOMOISOTWISTANE-3-CARBOXYLIC ACID ESTERS AND A PROCESS FOR PRODUCING THE SAME

BACKGROUND OF THE INVENTION

This invention relates to novel 4-homoisotwistane-3-carboxylic acid esters and a process for producing the same.

DESCRIPTION OF THE PRIOR ART

Heretofore, it has generally been known that various derivatives of adamantane, which is a cage-molecular hydrocarbon, are effective in the prophylaxis of influenza A2 and in the treatment of Parkinson's disease and the like.

SUMMARY OF THE INVENTION

The present inventors have examined a wide variety of 4-homoisotwistane (tricyclo[5.3.1.0$^{3,8}$] undecane) derivatives which are cage-molecular hydrocarbons of the same nature as adamantane and, as a result, have found that novel 4-homoisotwistane-3-carboxylic acid esters, represented by the following general formula (I), possess superior antiviral effects:

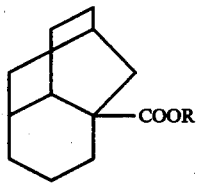

(I)

wherein R represents a 1-22C straight or branched alkyl or alkenyl group, or a monocyclic or polycyclic cycloalky group. Based on this finding, the present invention has been accomplished.

It is therefore, one object of this invention to provide novel 4-homoisotwistane-3-carboxylic acid esters of the formula [I] possessing superior antiviral activity.

Another object of this invention is to provide a process for producing 4-homoisotwistane-3-carboxylic acid esters of the formula [I].

According to the present invention, 4-homoisotwistane-3-carboxylic acid esters of the formula [I] are produced by reacting 4-homoisotwistane-3-carboxylic acid or its halides of the formula [II] with alcohols of the formula [III], as shown by the following reaction formula:

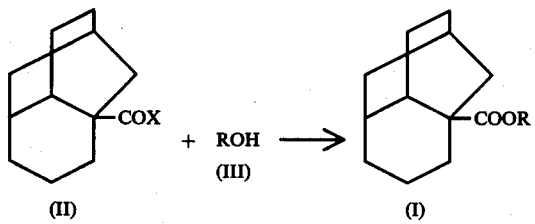

wherein X represents a chlorine or bromine atom, or a hydroxyl group and R is the same as described above.

The starting compound of this invention, 4-homoisotwistane-3-carboxylic acid is produced by reacting 4-homoisotwistane with t-butyl alcohol and formic acid or carbon monoxide in the presence of sulfuric acid.

All known esterification methods are applicable to the present process of forming 4-homoisotwistane-3-carboxylic acid esters from 4-homoisotwistane-3-carboxylic acid.

One typical method comprises reacting 4-homoisotwistane-3-carboxylic acid with alcohols with or without solvent immiscible with water, such as benzene, toluene and the like in the presence of an acid or base as a catalyst. Another method comprises reacting 4-homoisotwistane-3-carbonyl halide with alcohols with or without an inert solvent in the absence or presence of a base, such as N,N-dimethylaniline, pyridine, quinoline, triethylamine, tributylamine and the like.

When the first mentioned method is employed, an equivalent amount of alcohol to 4-homoisotwistane-3-carboxylic acid may be used. To accelerate the reaction, more than 3-fold moles of alcohols are preferably used. When the alcohols to be used have lower boiling points and lower viscosities, they can be used as the solvent by themselves. In order to remove water formed in the reaction system, however, the mixture may be refluxed with a small amount of benzene, toluene and the like. As a result, acceleration of the reaction is accomplished.

When the alcohols to be used have high boiling points or are solids, a solvent capable of forming an azeotropic mixture with water such as benzene, toluene and the like is preferably used.

The reaction may be conducted with other solvents instead of the above mentioned ones, such as hexane, methylcyclohexane and the like. It is to be noted, however, that the use of these solvents is not so preferable from the view-point of yield and required reaction time. The use of benzene or toluene as mentioned above generally affords better results.

The acid to be used as a catalyst generally includes mineral acids such as sulfuric acid, and organic acids such as p-toluenesulfonic acid. The basic catalyst to be used includes oxides or hydroxides of alkali metals and alkaline earth metals.

The reaction may be performed at a temperature ranging from +50° to +200° C, and more preferably, a higher temperature over this range is selected to accelerate the reaction. Generally, the reaction is effected at the boiling point of a solvent such as benzene, toluene and the like or at the boiling point of an alcohol to be used.

When the second mentioned method is employed, an equivalent amount of alcohol to 4-homoisotwistane-3-carbonyl halide is used, and the mixture is stirred at room temperature in an inert solvent such as, an ether or a hydrocarbon.

However, when alkenyl alcohols are used, there is a possibility that the hydrogen halide formed will add to alkenyl alcohols to produce by-products. In order to eliminate this side reaction, there may be required a copresence of an organic base such as triethylamine, tributylamine, pyridine, picoline, quinoline and the like. Reaction time required may be shortened by using a higher temperature. However, there is no need of application of heat in order to avoid the above side reaction since the reaction generally proceeds quickly at a lower temperature.

4-Homoisotwistane-3-carboxylic acid esters of the formula [I] exert extremely excellent effects on monolayer cultures of chick embryo fibroblasts cells against Newcastle disease viruses among Para-myxovirus belonging to RNA type virus and present less cytotoxicity at their effective concentrations.

The present compounds exhibit an apparent inhibition of viral growth at 1/30 to 1/5 the concentration of adamantylamine hydrochloride which is well known as an anti-influenza virus agent.

These findings are based on the following experimental results.

After chick embryo fibroblast cells were cultured in a test tube for 2 to 3 days, the medium was inoculated with Newcastle disease viruses of about 128 HAU(-Hemagglutination Units). To the upper layer were added a culture medium of the step-wise dilution system containing the following compounds, then the resulting mixture was cultivated at 37° C for 48 hours and the effects were evaluated based on the hemagglutination reaction.

The results obtained are shown in Table 1.

Table 1

| Compounds | Minimum growth inhibitory concentration (μg/ml) | Minimum toxic concentration (μg/ml) |
|---|---|---|
| 4-Homoisotwistane-3-carboxylic acid methyl ester | 16 | 31 |
| 4-Homoisotwistane-3-carboxylic acid n-octyl ester | 100 | 150 |
| Adamantylamine hydrochloride (Control) | 500 | 250 |

The invention is described in further detail with reference to Examples which are illustrative of, but not restrictive of the invention.

EXAMPLE 1

4-Homoisotwistane-3-carboxylic acid methyl ester (Formula I, R=CH$_3$):

To a solution of 9.7g (50m moles) of 4-homoisotwistane-3-carboxylic acid in 50 ml of methanol was added 0.1ml of conc. sulfuric acid, and the resulting mixture was refluxed for 5 hours. After the completion of the reaction, to the mixture was added 50ml of water. The resulting mixture was extracted three times with 20ml of ether and the extract was freed of solvent by distillation. The residue obtained was fractionated by vacuum distillation to afford 7.9g (yield 76%) of 4-homoisotwistane-3-carboxylic acid methyl ester as a colourless oil having a boiling point of 87.5° C/0.9mmHg.

$\eta_D^{24} = 1.4887$

Elemental Analysis: as C$_{13}$H$_{20}$O$_2$. Calculated (%) : C : 75.0; H: 9.7. Found (%) : C : 74.6; H: 9.9.

ir (liquid film, cm$^{-1}$)

1730 (C=O), 1210, 1190, 1170 pmr (solvent: CCl$_4$; internal standard: TMS, δ)

3.64 (singlet, 3H,

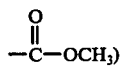

2.6–0.8 (multiplet, 17H)

ms m/e (relative strength)

208 (10, M+), 150 (13), 149(100), 107 (7), 93 (9), 91 (6), 81 (14), 79 (10), 67 (21), 41 (7)

EXAMPLE 2

4-Homoisotwistane-3-carboxylic acid butyl ester (Formula I, R=n-C$_4$H$_9$):

A mixture of 2.6g (12.2m moles) of 4-homoisotwistane-3-carbonyl chloride and 2.7g (36.6m moles) of n-butanol was stirred at room temperature for about 1 hour. After the completion of the reaction, the mixture was fractionated by vacuum distillation to afford 2.78g (Yield 91% ) of 4-homoisotwistane-3-carboxylic acid butyl ester as a colourless oil having a melting point of 110° C/0.5mmHg.

$\eta_D^{24} = 1.4902$

Elemental Analysis: as C$_{16}$H$_{26}$O$_2$. Calculated (%) : C: 76.8; H:10.5. Found (%) : C: 76.7; H:10.5.

ir (liquid film, cm$^{-1}$)

1720(C=O), 1205, 1190, 1170 pmr (solvent: CCl$_4$; internal standard: TMS, δ)

4.0 (triplet,

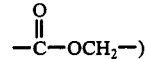

2.5–0.9 (complex multiplet)

ms m/e (relative strength)

250(3, M+), 195(6), 149(100), 107(6), 93(7), 81(13), 67(25), 41(14), 29(12), 18(20)

EXAMPLE 3

4-Homoisotwistane-3-carboxylic acid n-octyl ester (Formula I, R=n-C$_8$H$_{17}$):

To a mixture of 9.7g(50m moles) of 4-homoisotwistane-3-carboxylic acid, 19.5g (150m moles) of n-octyl alcohol and 50ml of benzene was added 0.5ml of conc. sulfuric acid and the resulting mixture was refluxed for about 5 hours, while water formed during the course of the reaction was continually removed. After the completion of the reaction, to the mixture was added 50ml of water. The resulting mixture was extracted three times with 20ml of benzene and the extract was freed of solvent by distillation. The residue obtained was fractionated by vacuum distillation to afford 12.5g (yield 82%) of 4-homoisotwistane-3-carboxylic acid n-octyl ester as a colourless oil having a boiling point of 131° C/0.15mmHg.

$\eta_D^{22} = 1.4842$

Elemental Analysis: as C$_{20}$H$_{34}$O$_2$. Calculated (%): C: 78.4; H: 11.2. Found (%): C: 78.6; H: 11.3.

ir (liquid film; cm$^{-1}$)

1720(c=O), 1205, 1190, 1170 pmr (solvent: CCl$_4$; internal standard: TMS, δ)

4.0 (multiplet,

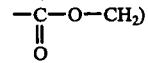

2.5–0.9 (complex multiplet)

ms m/e (relative strength)

306(1.8, M+), 195(17), 150(14), 149(100), 81(14) 67(24), 55(10), 43(13), 41(18), 29(9), 18(13)

EXAMPLE 4

4Homoisotwistane-3-carboxylic acid cyclohexyl ester (Formula II, R=$C_6H_{11}$):

4-Homoisotwistane-3-carboxylic acid was reacted with cyclohexanol under the same reaction conditions as described in Example 3 to afford an oily product (yield 89%) having a boiling point of 147° C/1mmHg.

$\eta_D^{25} = 1.5058$

Elemental Analysis : as $C_{18}H_{28}O_2$. Calculated (%) : C: 78.2; H:10.2. Found (%) : C: 77.9; H:10.2.

ir (liquid film, cm$^{-1}$)
 1720(C=O), 1210, 1200, 1180 pmr (solvent : $CCl_4$; internal standard : TMS, δ)
 4.7 (broad singlet, 1H)
 2.5~1.0 (multiplet, 27H)

ms m/e (relative strength)
 276(1.5, M+), 195(45), 150(13), 149(100), 83(12), 81(15) 79(12), 67(31), 55(18), 41(19), 28(11)

EXAMPLE 5

4-Homoisotwistane-3-carboxylic acid tetrahydrodicyclopentadiene-exo-2-yl ester (Formula II, R =  ):

An amount of 106g (5m moles) of 4-homoisotwistane-3-carbonyl chloride was reacted, with stirring, with 0.76g (5ml) of 2-exo-hydroxy-exo-tetrahydrodicyclopentadiene represented by the following formula (IV)

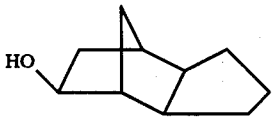

(IV)

in 10ml of ether for about 3 hours in a similar manner as in Example 2. After the completion of the reaction, the mixture was freed of solvent by distillation and the residue was distilled under reduced pressure to afford 1.33g (yield 81%) of 4-homoisotwistane-3-carboxylic acid tetrahydrodicyclopentadiene-exo-2-yl ester as a colorless oil having a boiling point of 203° C/1.5mmHg.

$\eta_D^{24} = 1.5227$

Elemental Anaysis : as $C_{22}H_{32}O_2$. Calculated (%) : C: 80.4; H: 9.8. Found (%) : C: 80.1; H: 10.2.

ir (liquid film, cm$^{-1}$)
 1720(C=O), 1220, 1200, 1190, 1170, pmr (solvent : $CCl_4$; internal standard TMS, δ)
 4.5(multiplet, 1H), 2.5–0.9(multiplet, 31H)

ms m/e (relative strength)
 328(0.8,M+), 260(1.6), 206(1.4), 195(12), 149(100), 135(57), 134(21), 93(15), 81(19), 79(18), 67(62), 66(30), 41(22), 18(24)

Reference Example 1

Synthesis of 4-homoisotwistane -3- carboxylic acid

To the mixture of 15g (0.1 mole) of 4-homoisotwistane, 100ml of carbon tetrachloride and 450g of 95% sulfuric acid was added dropwise over a period of 2.5 hours with ice-cooling a solution of 55g (1.20 moles) of 99% formic acid in 30g (0.41 mole) t-butyl alcohol, while the temperature was kept at 17° C. After completion of the dropwise addition, the mixture was further stirred at room temperature for 3 hours.

The reaction mixture was poured into 1Kg of crushed icewater to separate the organic layer and the aqueous layer was extracted with carbon tetrachloride. The combined organic layer was washed with water and extracted three times with 1.5% sodium hydroxide solution. This extract was adjusted to pH1~2 with diluted sulfuric acid and the resulting solution was extracted with carbon tetrachloride. The extract was dried over anhydrous sodium sulfate and fractionated by vacuum distillation to afford 12.5g (yield 63%) of crude 4-homoisotwistane-3-carboxylic acid having a boiling point of 135°–140° C/0.9mmHg. This product was allowed to stand to give solidified white crystals. These crystals were sublimed under reduced pressure to give a pure product having a melting point of 95°–96° C.

Elemental Analysis: as $C_{12}H_{18}O_2$. Calculated (%) : C: 74.2; H: 9.3. Found (%) : C: 74.5; H: 9.5.

ir (liquid film, cm$^{-1}$)
 3400-2900 (broad absorption OH)
 1700(C=O)

pmr (solvent: $CDCl_3$; internal standard : TMS,δ)
 2.6–0.8 (complex multiplet, 17H)
 10.20 (1H, disappearance by treatment with deuterium oxide)

ms m/e 194(M+)

Reference Example 2

Synthesis of 4-homoisotwistane-3-carbonyl chloride

4-Homoisotwistane-3-carboxylic acid chloride was prepared with ease by reacting 4-homoisotwistane-3-carboxylic acid with thionyl chloride.

$\eta_D^{22} = 1.5238$

Boiling point: 96°–97° C/0.9mmHg

Elemental Analysis: as $C_{12}H_{17}OCl$. Calculated (%): C: 67.8; H: 8.1; Cl: 16.7. Found (%): C: 68.0; H: 8.3; Cl: 16.2.

Reference Example 3

Synthesis of 4-homoisotwistane-3-carbonyl bromide

4-Homoisotwistane-3-carboxylic acid was reacted with thionyl bromide under the same conditions as in Reference Example 2. After the completion of the reaction, the desired product was obtained by fractional distillation. $\eta_D^{20} = 1.5511$ Boiling point : 128° C/3mmHg Elemental Analysis : as $C_{12}H_{17}OBr$. Calculated (%) : C: 56.0; H: 6.7; Br:31.1. Found (%) : C: 55.6; H: 6.8; Br:30.6.

What is claimed as new and intended to be covered by Letters Patent is:

1. 4-Homoisotwistane-3-carboxylic acid esters of the formula:

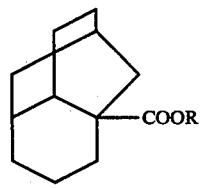

wherein R represents a $C_{1-22}$ straight or branched alkyl or alkenyl group, or a monocyclic or polycyclic cycloalkyl group.

2. 4Homoisotwistane-3-carboxylic acid methyl ester.

3. 4-Homoisotwistane-3-carboxylic acid butyl ester.

4. 4-Homoisotwistane-3-carboxylic acid octyl ester.

5. 4-Homoisotwistane-3-carboxylic acid tetrahydrodicyclopentadiene-exo-2yl ester.

* * * * *